United States Patent [19]
Ishida et al.

[11] Patent Number: 5,631,014
[45] Date of Patent: May 20, 1997

[54] OXAZOLINE DERIVATIVES, INSECTICIDAL AND MITICIDAL COMPOSITION, AND METHOD FOR CONTROLLING INSECTS AND MITES

[75] Inventors: Tatsuya Ishida, Nagano; Chiharu Morikawa, Suzaka; Tatsufumi Ikeda, Nagano; Junji Suzuki, Suzaka; Yasuaki Hariya, Kawaguchi; Yasuo Kikuchi, Nagano, all of Japan

[73] Assignee: Yashima Chemical Industry Co., Ltd., Kanagawa-ken, Japan

[21] Appl. No.: 471,233

[22] Filed: Jun. 6, 1995

[30] Foreign Application Priority Data

Jun. 9, 1994 [JP] Japan .................... 6-150637

[51] Int. Cl.$^6$ ................................ A01N 25/02
[52] U.S. Cl. .............. 424/405; 424/409; 424/419; 424/421; 514/374; 514/365
[58] Field of Search .................... 424/408, 409, 424/405; 514/365, 374, 63

[56] References Cited

U.S. PATENT DOCUMENTS 5,141,948  8/1992  Miyamoto et al. ............... 514/365

FOREIGN PATENT DOCUMENTS 57-501962  11/1982  Japan .
3-232867   10/1991  Japan .
6-48907     2/1994  Japan .
82/02046    6/1982  WIPO .

OTHER PUBLICATIONS

Vorbrüggen et al., "A Simple Synthesis Of Δ$^2$–Oxazolines, Δ$^2$–Oxazines, Δ$^2$–Thiazolines And Δ$^2$–Imidazolines", Tetrahedron Letters, vol. 22, No. 45, pp. 4471–4474, 1981.

Bazyl et al., "Theoretical Study Of The Spectral–Luminescence Properties Of Oxazol–5–One Derivatives", Chemical Abstracts vol. 98, No. 19, 1983, Abstract, 98:160087k; and Izu. Vyssh. Uchebn. Zaued., Fiz. 1983, 26(1), 108–9 (Russian).

Tsuge et al., "Regioselective Cycloadditions Of N–Protonated Azomethine Ylides And 2–Azaallyl Anions Generated From N–(Silylmethyl) Thioimidates, Synthetic Equivalents Of Nonstabilized Nitrile Ylides", J. Org. Chem., pp. 2523–2530, 1987.

*Primary Examiner*—Neil S. Levy
*Attorney, Agent, or Firm*—Wenderoth, Lind & Ponack

[57] ABSTRACT

This invention provides an insecticidal and miticidal agent which contains as an effective ingredient an oxazoline derivative represented by the formula

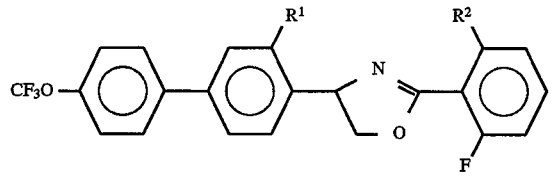

wherein, $R^1$ represents a fluorine atom, a chlorine atom, a $C_1$ to $C_3$ alkyl group or a $C_1$ to $C_3$ alkoxy group, and $R^2$ represents a fluorine atom or a chlorine atom.

The insecticidal and miticidal agent exhibits an excellent insecticidal and miticidal activity against harmful insects and mites parasitic on useful plants.

12 Claims, No Drawings

OXAZOLINE DERIVATIVES, INSECTICIDAL AND MITICIDAL COMPOSITION, AND METHOD FOR CONTROLLING INSECTS AND MITES

This invention relates to an insecticidal and miticidal agent for control of plant-parasitic insects and mites which contains as an effective ingredient a certain kind of an oxazoline derivative.

Certain oxazoline derivatives, for example 2,4-diphenyl-2-oxazoline compounds are already reported [see Tetrahedron Letters, Vol. 22 No. 45, pp 4471 to 4474 (1981); Chemical Abstracts, Vol. 98 No. 19, 160087k (1983); J. Org. Chem., 52, 2523 to 2530 (1987), etc.]. Further, although Japanese Patent Official Announcement 501962/1982 discloses $\Delta^2$-N-heterocyclic compounds useful as intermediates for preparation of pharmaceuticals or as antidiabetic drugs, it does not disclose usefulness as agents for controlling pests harmful to agrohorticultural crops at all.

Further, it is disclosed in Japanese Laid-Open Patent Publication No. 232867/1991 (Corres. to EP-A-432661 and U.S. Pat. No. 5,141,948) that 2,4-diphenyl-2-oxazoline compounds have an insecticidal and miticidal effect against harmful pests which parasitize useful plants, and among compounds specifically disclosed are included those having a considerably excellent insecticidal and miticidal activity. However, in recent years, substances exerting a high activity at a small dose a redesired in view of safety, economical efficiency, etc., and when such a situation is considered, the above known compounds are not always satisfactory in point of insecticidal and miticidal activity, etc., and development of compounds which are safe and have higher activities is strongly desired.

On the other hand, it is disclosed in Japanese Laid-Open Patent Publication No. 48907/1994 (Corres. to EP-A-645085) that certain 2,4-diphenyl-2-oxazoline compounds are useful for control of mites parasitic on animals and parasitic on dwelling environment, but it does not disclose at all about effects of these compounds on plant-parasitic harmful insects and mites.

The present inventors had synthesized many compounds for obtaining compounds exerting a high insecticidal and miticidal activity at a small dose against harmful insects and mites which parasitize useful plants, and had investigated their insecticidal and miticidal activities, and now found that among 2,4-diphenyl-2-oxazoline compounds, particularly certain oxazoline derivatives represented by the following formula (I)

① exert a strong insecticidal and miticidal activity even at an extremely low concentration against harmful pests which parasitize useful plants, ② have a remarkable insecticidal and miticidal activity even against resistant harmful pests whose susceptibility to various chemicals was lowered, and ③ exhibit only low toxicity on warm-blooded animals and are extremely safe, and completed this invention.

Thus, according to this invention, there is provided an insecticidal and miticidal agent for control of plant-parasitic insects or mites which contains as an effective ingredient an oxazoline derivative represented by the formula

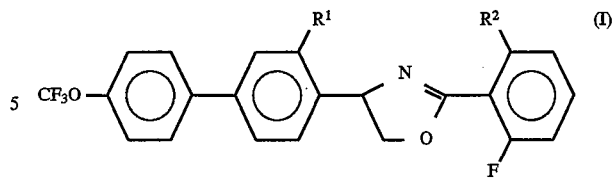

wherein, $R^1$ represents a fluorine atom, a chlorine atom, a $C_1$ to $C_3$ alkyl group or a $C_1$ to $C_3$ alkoxy group, and $R^2$ represents a fluorine atom or a chlorine atom.

The $C_1$ to $C_3$ alkyl group and the $C_1$ to $C_3$ alkoxy group represented by $R^1$ in the above formula (I) can be any of straight-chain or branched chain ones, and include methyl, ethyl, n-propyl, isopropyl; methoxy, ethoxy, n-propoxy and isopropoxy.

Preferred among the compounds of the above formula (I) are compounds of the formula (I) wherein $R^1$ represents a fluorine atom, a chlorine atom or a methyl group, and $R^2$ represents a fluorine atom, and particularly preferred are compounds of the formula (I) wherein R1 represents a methyl group, and $R^2$ represents a fluorine atom.

Part of the compounds of the formula (I) are known (see, for example, Japanese Laid-Open Patent Publication No. 48907/1994 (Corres. to EP-A-645085)), and those undisclosed in literatures can be prepared in the same manner as in the known compounds (see the later-described Preparation example 1).

The insecticidal and miticidal agent of this invention displays an excellent insecticidal and miticidal effect (including an ovicidal effect) against various harmful insects and mites parasitic on useful plants, specifically vegetables, fruit trees, flowering plants, garden trees, etc., for example, aphids such as *Myzus persicae, Aphis gossypii, Lipaphis pseudobrassicae, Eriosoma lanigerum, Nippolachnus piri* and *Hyalopterus pruni*: thrips such as *Scirtothrips dorsalis, Thrips palmi, Franklinleila occidentalis* and *Ponticulothrips diospyrosi*: lepidopterons such as *Plutella xylostella, Pieris rapae, Marnestera brassicae, Spodoptera litura, Spodoptera exigua, Autographa nigrisigna, Homona magnanima, Adoxophyes spp., Phyllonorycter ringoniella, Lyonetia clerkella, Phyllocnistis citrella, Grapholitha molesta, Carposina niponensis, Chilo suppressalis* and *Ostrinia furnacalis*: and mites such as *Tetranychus urticae, Tetranychus kanzawai, Panonychus citri* and *Panonychus ulmi*. Moreover, the insecticidal and miticidal agent of this invention does not cause such phytotoxicity that causes a problem on useful plants.

The insecticidal and miticidal agent of this invention can take various formulation forms, and for example, can be applied in formulation forms such as powders, granules, wettable powders, emulsions, flowable agents, microcapsules, aerosols, smoking chemicals and poison baits. Such formulations can, usually, be prepared by appropriately mixing an effective amount of an active compound of the above formula (I) with solid or liquid carriers or diluents, surface active agents, and agrohorticulturally acceptable other adjuvants for formulations, and formulating the mixtures into desired formulation forms according to conventional processes, respectively.

Usable solid carriers or diluents include, for example, plant powders such as soybean meal and wheat flour; mineral fine powders such as talc, bentonite and clay, and liquid carriers or diluents include, for example, xylene, toluene, benzene, cyclohexane, acetone, alcohols, mineral oils, petroleum and water, Surface active agents compoundable according to necessity include, for example, nonionic-type polyoxyalkylene alkyl ether, polyoxyalkylene aryl ether, polyoxyalkylene fatty acid esters and polyoxyal kylenesorbitan fatty acid esters; and anionic-type alkylaryl sulfate ester salts and polyoxyalkylenealkylaryl sulfate ester salts, or their mixtures.

The active compounds of the formula (I) in this invention can be formulated into formulation forms such as wettable powders, granules, powders, emulsions, flowable agents, microcapsules, aerosols, smoking chemicals and poison baits, according to agricultural chemical formulation processes known per se using the foregoing compounding components. Preferred among them are emulsions, flowable agents and wettable powders, and emulsions are particularly preferred.

The compounding ratios of the active compounds of the formula (I) in these formulations can widely be varied depending on the kind of the compounds, the formulation forms, etc., but are generally suitable in the range of 0.01 to 80 wt. %, and preferably, according to respective formulation forms, for example in the case of emulsions, wettable powders and flowable agents, etc., they can contain the compounds of the formula (I) at concentrations within the range of 0.01 to 50 wt. %, more preferably 0.1 to 20 wt. %, respectively, and in the case of powders and granules, etc., they can contain the compounds of the formula (I) at concentrations within the range of 0.01 to 20 wt. %, more preferably 0.1 to 10 wt. %, respectively. The wettable powders, emulsions and flowable agents can be applied after being diluted with water into suspensions or emulsions having predetermined concentrations, and the powders and granules can be applied as such.

The insecticidal and miticidal agents of this invention may be used as mixtures or in combinations with other agricultural chemicals such as, for example, insecticides, miticides, fungicides and plant growth regulators.

Formulations containing the compounds of the formula (I) of this invention can be used for controlling insects and/or mites which do harm to agrohorticultural crops by, for example applying them directly to imagoes, larvae or nits of the insects or mites, or applying them to locuses which these imagoes, larvae or nits inhabit. The application quantity of the compounds of the formula (I) at this time can suitably be varied depending on the kind of active compounds, the formulation forms, the degrees of occurrence of the pests, etc. However, in general, the application quantity can be within the range of 1 to 10,000 g, preferably 10 to 1,000 g per hectare, and specifically, for example, in the case of the above emulsions, wettable powders and flowable agents, etc., they can usually be diluted 1,000 to 10,000-fold and applied at ratios of 1,000 to 10,000 liters per hectare, and in the case of the powders and the granules, etc., it is usually proper to apply them at ratios of 2 to 40 kg per hectare.

The compounds of the formula (I) used as effective ingredients in this invention can, for example, be prepared by the three steps shown in the following reaction formulae.

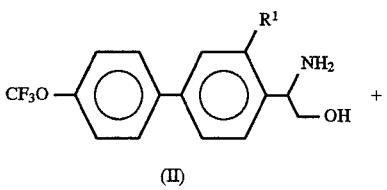

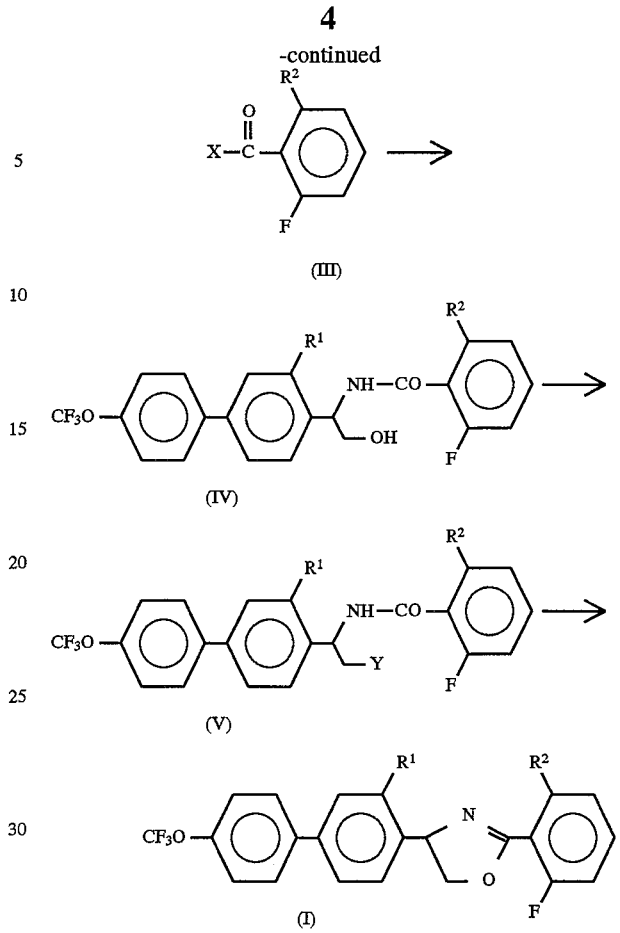

wherein $R^1$ and $R^2$ are as defined above, and X and Y represent halogen atoms.

In the above reaction formulae, the synthesis of an intermediate amidoethanol (IV) in the first step can be carried out by reacting a compound (II) with a compound (III) in a solvent or without any solvent, and preferably in the presence of a base for accelerating the reaction.

The solvent is not particularly limited so long as it is not directly involved with this reaction, and includes, for example, ethers (diethyl ether, tetrahydrofuran, dioxane, diglyme, etc.); aromatic hydrocarbons (benzene, toluene, xylene, etc.); halogenated hydrocarbons (dichloromethane, chloroform, carbon tetrachloride, dichloroethane, etc.); ketches (acetone, methyl ethyl ketone, etc.); and mixtures of these solvents. As the base, there can be used, without any particular limitation, for example, inorganic bases such as sodium hydroxide, potassium hydroxide and potassium carbonate; and tertiary organic bases such as triethylamine, N,N-dimethylaniline, pyridine and 4-N,N-dimethylaminopyridine.

The reaction temperature is not particularly limited, but in general, can be a temperature range of an ice-cooling temperature to the boiling point of the solvent used, and particularly preferably within the range of 0° C. to 30° C. The reaction time can usually be on the order of 1 to 6 hours.

The synthesis of an intermediate amidoethyl halide (V) in the second step can be carried out by reacting the compound (IV) with thionyl halide (SOY$_2$: Y represents a halogen atom) in a solvent or without any solvent, and is preferably carried out with heating for accelerating the reaction.

The solvent is not particularly limited so long as it is not directly involved with this reaction, and includes, as in the above reaction, ethers; aromatic hydrocarbons; ketches; and mixtures of these solvents.

The reaction temperature is not particularly limited, but in general, can be a temperature range of an ice-cooling temperature to the boiling point of the solvent used, and particularly preferably within the range of 50° C. to 80° C. The reaction time can usually be on the order of 1 to 4 hours.

In the third step, a compound (I) can be prepared by treating an intermediate compound (V) in a solvent or without any solvent to cyclize it, and is preferably reacted with heating for accelerating the reaction.

The solvent is not particularly limited so long as it is not directly involved with this reaction, and includes, as in the above reactions, ethers; aromatic hydrocarbons; alcohols such as methanol and ethanol; and mixtures of these solvents, but it is preferred to use methanol or ethanol.

The reaction temperature is not particularly limited, but in general, can be a temperature range of an ice-cooling temperature to the boiling point of the solvent used, and particularly preferably within the range of 40° C. to 80° C. The reaction time can usually be on the order of 0.3 to 2 hours.

There can be used as the base the above-mentioned inorganic bases, but preferred are sodium hydroxide and potassium hydroxide.

Compounds of the formula (I) prepared according to the foregoing can, for example, be subjected to usual post-treatments such as extraction, filtration and concentration, and, if needed, further purified appropriately by means known per se such as recrystallization and various chromatographies.

This invention is further specifically described below according to preparation examples, formulation examples and test examples.

<Preparation Example>

Preparation example 1: Preparation of a compound of the formula (I) 2-(2,6-Difluorophenyl)-4-{2-methyl-4-(4-trifluoromethoxyphenyl)phenyl}-2-oxazoline (Compound No. 1)

To a mixture of 2.7 g (9 mmol) of 2-amino-2-{2-methyl-4-(4-trifluoromethoxyphenyl)phenyl}-ethanol, 1.5 g (15 mmol) of triethylamine and 50 ml of tetrahydrofuran was gradually added dropwise, under ice-cooling and stirring, a mixture of 1.6 g (9 mmol) of 2,6-difluorobenzoyl chloride and 10 ml of tetrahydrofuran. The mixture was further stirred at room temperature for 3 hours, the reaction solution was filtered, and the filtrate was concentrated under reduced pressure.

To this mixture were added 30 ml of benzene and 1.2 g (10 mmol) of thionyl chloride, and the mixture was refluxed for 3 hours under stirring on a water bath. The reaction solution was brought back to room temperature and then concentrated under reduced pressure.

To this concentrate were added 50 ml of methanol and 0.9 g of potassium hydroxide, and the mixture was stirred at 70° C. for one hour. After a post-treatment, the mixture was purified by column chromatography (moving phase n-hexane: ethyl acetate=5: 1) to give 2.7 g of 2-(2,6-difluorophenyl)-4-{2-methyl-4-(4-trifluoromethoxyphenyl)-phenyl}-2-oxazoline (colorless crystals, m.p. 78.5°–79.0° C., yield 69.3 %).

$^1$H-NMR (60 MHz, CDCl$_3$, TMS) δ(ppm) : 2.3 (3H, s), 4.1 (1H, t, J=8Hz), 4.8 (1H, t, J=8Hz), 5.6 (1H, t, J=9Hz), 6.6–7.6 (10H, m) IR: 1670 cm$^{-1}$ (C=N).

The compounds of the formula (I) shown in the following Table 1 were prepared in the same manner as above.

TABLE 1

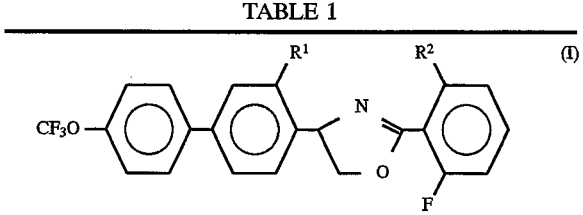

| Compound No. | R$^1$ | R$^2$ | Physical property value (refractive index N$_D^{25}$ or melting point) |
|---|---|---|---|
| 1 | Methyl group | Fluorine atom | mp = 78.5–79.0° C. |
| 2 | Methyl group | Chlorine atom | N$_D^{25}$ = 1.5737 |
| 3 | Ethyl group | Fluorine atom | N$_D^{25}$ = 1.5601 |
| 4 | Ethyl group | Chlorine atom | N$_D^{25}$ = 1.5697 |
| 5 | n-Propyl group | Fluorine atom | N$_D^{25}$ = 1.5572 |
| 6 | n-Propyl group | Chlorine atom | N$_D^{25}$ = 1.5665 |
| 7 | i-Propyl group | Fluorine atom | N$_D^{25}$ = 1.5546 |
| 8 | i-Propyl group | Chlorine atom | N$_D^{25}$ = 1.5642 |
| 9 | Methoxy group | Fluorine atom | N$_D^{25}$ = 1.5610 |
| 10 | Methoxy group | Chlorine atom | mp = 89.5–91.0° C. |
| 11 | Ethoxy group | Fluorine atom | N$_D^{25}$ = 1.5568 |
| 12 | Ethoxy group | Chlorine atom | N$_D^{25}$ = 1.5658 |
| 13 | n-Propoxy group | Fluorine atom | N$_D^{25}$ = 1.5502 |
| 14 | n-Propoxy group | Chlorine atom | N$_D^{25}$ = 1.5593 |
| 15 | i-Propoxy group | Fluorine atom | N$_D^{25}$ = 1.5514 |
| 16 | i-Propoxy group | Chlorine atom | N$_D^{25}$ = 1.5603 |
| 17 | Fluorine atom | Fluorine atom | mp = 70.5–71.5° C. |
| 18 | Fluorine atom | Chlorine atom | N$_D^{25}$ = 1.5753 |
| 19 | Chlorine atom | Fluorine atom | mp = 53.5–54.5° C. |
| 20 | Chlorine atom | Chlorine atom | N$_D^{25}$ = 1.5783 |

<Formulation Example>

Formulation Example 1: Emulsion

10 Wt. parts of a compound of the formula (I), 12 wt. parts of polyoxyethylene nonylphenyl ether and 78 wt. parts of xylene are uniformly mixed to give an emulsion.

Formulation Example 2: Wettable Powder

10 Wt. parts of a compound of the formula (I), 5 wt. parts of sodium dodecylbenzenesulfonate, 3 wt. parts of polyoxyethylene nonylphenyl ether, 30 wt. parts of clay and 52 wt. parts of diatom earth are uniformly mixed and ground to give a wettable powder.

Formulation Example 3: Flowable Agent

5 Wt. parts of polyoxyethylene styrylphenyl ether sulfate salt, 3 wt. parts of smectite mineral substance and 62 wt. parts of water were made into a uniform solution, 10 wt. parts of a compound of the formula (I) is added, and the mixture is sufficiently stirred and wet-ground using a sand mill. Then, 20 wt. parts of 1% aqueous Xanthangum solution was added, and the mixture is sufficiently stirred to give a flowable agent.

<Test Example>

The known compounds used as controls in the following test examples are shown in the following Table 2. The compound numbers described in the remarks column in this table are compound numbers described in Japanese Laid-Open Patent Publication No. 232867/1991.

TABLE 2

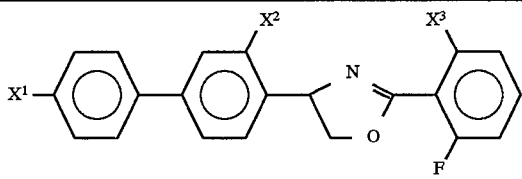

| Compound No. | $X^1$ | $X^2$ | $X^3$ | Remarks |
|---|---|---|---|---|
| Control 1 | t-Butyl group | Chlorine atom | Fluorine atom | Compound No. 175 |
| Control 2 | t-Butyl group | Chlorine atom | Chlorine atom | Compound No. 176 |
| Control 3 | Ethyl group | Fluorine atom | Fluorine atom | Compound No. 194 |
| Control 4 | Ethyl group | Fluorine atom | Chlorine atom | Compound No. 195 |
| Control 5 | $OCF_3$ group | Hydrogen atom | Fluorine atom | Compound No. 198 |
| Control 6 | $OCF_3$ group | Hydrogen atom | Chlorine atom | Compound No. 199 |
| Control 7 | i-Propyl group | Chlorine atom | Fluorine atom | Compound No. 202 |
| Control 8 | i-Propyl group | Chlorine atom | Chlorine atom | Compound No. 203 |
| Control 9 | n-Propyl group | Chlorine atom | Fluorine atom | Compound No. 206 |
| Control 10 | Chlorine atom | Ethoxy group | Fluorine atom | Compound No. 213 |
| Control 11 | Chlorine atom | Ethoxy group | Chlorine atom | Compound No. 214 |
| Control 12 | 1-Ethylpropyl group | Chlorine atom | Fluorine atom | Compound No. 228 |
| Control 13 | 1-Ethylpropyl group | Chlorine atom | Chlorine atom | Compound No. 229 |
| Control 14 | n-Propyl group | Ethoxy group | Fluorine atom | Compound No. 230 |
| Control 15 | n-Propyl group | Ethoxy group | Chlorine atom | Compound No. 231 |
| Control 16 | n-Propyl group | Fluorine atom | Fluorine atom | Compound No. 232 |
| Control 17 | n-Propyl group | Fluorine atom | Chlorine atom | Compound No. 233 |
| Control 18 | n-Propyl group | Chlorine atom | Chlorine atom | Compound No. 234 |
| Control 19 | Ethyl group | Chlorine atom | Fluorine atom | Compound No. 238 |
| Control 20 | Ethyl group | Chlorine atom | Chlorine atom | Compound No. 239 |
| Control 21 | Chlorine atom | Chlorine atom | Fluorine atom | Compound No. 246 |
| Control 22 | Chlorine atom | Chlorine atom | Chlorine atom | Compound No. 247 |
| Control 23 | Chlorine atom | Ethoxy group | Fluorine atom | Compound No. 248 |
| Control 24 | Chlorine atom | Ethoxy group | Chlorine atom | Compound No. 249 |

Test Example 1: Inseticidal Test on Juveniles of *Myzus persicae*

Apterous embryonic female imagoes of *Myzus persicae* resistant to pyrethroid agents and organophosphorus agents were made to parasitize seedlings of a Chinese radish of the two-true leaf stage planted in cups in a ratio of 5 insects per seedling, allowed to larviposit for 3 days, and then removed. Chemicals of the stated concentrations (the emulsions of Formulation example 1 were diluted with water) were applied, respectively. The treated seedlings were put in a greenhouse, and 96 hours later insecticidal ratios were investigated. The test was carried out through three replicates for each section. The results are shown in the following Table 3.

TABLE 3

| Test compound | Insecticidal ratio (%)* | |
|---|---|---|
| | 10 ppm | 1 ppm |
| Compound No. 1 | 100% | 90% |
| Compound No. 2 | 100% | 85% |
| Compound No. 3 | 100% | 90% |
| Compound No. 4 | 100% | 95% |
| Compound No. 5 | 100% | 95% |
| Compound No. 6 | 100% | 75% |
| Compound No. 7 | 100% | 80% |
| Compound No. 8 | 100% | 95% |
| Compound No. 9 | 100% | 90% |
| Compound No. 10 | 100% | 75% |
| Compound No. 11 | 100% | 85% |
| Compound No. 12 | 100% | 95% |
| Compound No. 13 | 100% | 70% |
| Compound No. 14 | 100% | 80% |
| Compound No. 15 | 100% | 85% |
| Compound No. 16 | 100% | 80% |
| Compound No. 17 | 100% | 95% |
| Compound No. 18 | 100% | 90% |
| Compound No. 19 | 100% | 95% |
| Compound No. 20 | 100% | 80% |
| Compound No. Control 1 | 0% | 0% |
| Compound No. Control 2 | 0% | 0% |
| Compound No. Control 3 | 10% | 0% |
| Compound No. Control 4 | 0% | 0% |
| Compound No. Control 5 | 0% | 0% |
| Compound No. Control 6 | 0% | 0% |
| Compound No. Control 7 | 0% | 0% |
| Compound No. Control 8 | 10% | 0% |
| Compound No. Control 9 | 20% | 10% |
| Compound No. Control 10 | 0% | 0% |
| Compound No. Control 11 | 0% | 0% |
| Compound No. Control 12 | 0% | 0% |
| Compound No. Control 13 | 0% | 0% |
| Compound No. Control 14 | 0% | 0% |
| Compound No. Control 15 | 5% | 0% |
| Compound No. Control 16 | 0% | 0% |
| Compound No. Control 17 | 0% | 0% |
| Compound No. Control 18 | 5% | 0% |
| Compound No. Control 19 | 0% | 0% |
| Compound No. Control 20 | 10% | 0% |
| Compound No. Control 21 | 5% | 0% |
| Compound No. Control 22 | 0% | 0% |
| Compound No. Control 23 | 0% | 0% |
| Compound No. Control 24 | 0% | 0% |
| Control A** | 0% | 0% |
| Control B*** | 0% | 0% |

TABLE 3-continued

| Test compound | Insecticidal ratio (%)* | |
|---|---|---|
| | 10 ppm | 1 ppm |

$$*\text{Insecticidal ratio (\%)} = \frac{\text{Number of the parasite before application} - \text{Number of the parasite at the time of investigation}}{\text{Number of the parasite before application}} \times 100$$

**Control A = Permethrin

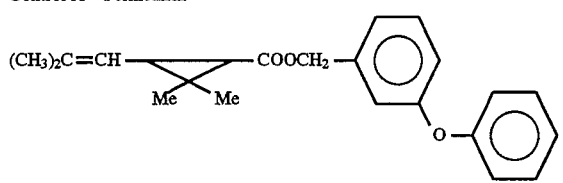

***Control B = Fenitrotion

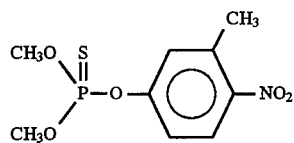

Test Example 2: Inseticidal Test on Larvae of *Plutella xylostella* Pieces of cabbage leaves (2 cm square) were immersed in liquids of chemicals of the stated concentrations (the emulsions of Formulation example 1 were diluted with water), respectively. After being air dried, the cabbage pieces were put, together with 15 each of hatched larvae of *Plutella xylostella* having resistance to chitin synthesis-inhibiting agents, in ice cream cups of diameter 9 cm, respectively. The cups were placed in a constant temperature chamber of 25 ° C., and 3 days later the insecticidal ratios were investigated. The test was carried out through three replicates for each section. The results are shown in the following Table 4.

TABLE 4

| Test compound | Insecticidal ratio (%)* | |
|---|---|---|
| | 10 ppm | 1 ppm |
| Compound No. 1 | 100% | 100% |
| Compound No. 2 | 100% | 100% |
| Compound No. 3 | 100% | 100% |
| Compound No. 4 | 100% | 100% |
| Compound No. 5 | 100% | 100% |
| Compound No. 6 | 100% | 100% |
| Compound No. 7 | 100% | 90% |
| Compound No. 8 | 100% | 95% |
| Compound No. 9 | 100% | 100% |
| Compound No. 10 | 100% | 100% |
| Compound No. 11 | 100% | 100% |
| Compound No. 12 | 100% | 95% |
| Compound No. 13 | 100% | 90% |
| Compound No. 14 | 100% | 95% |
| Compound No. 15 | 100% | 90% |
| Compound No. 16 | 100% | 85% |
| Compound No. 17 | 100% | 100% |
| Compound No. 18 | 100% | 100% |
| Compound No. 19 | 100% | 100% |
| Compound No. 20 | 100% | 100% |
| Compound No. Control 1 | 10% | 0% |
| Compound No. Control 2 | 0% | 0% |
| Compound No. Control 3 | 5% | 0% |
| Compound No. Control 4 | 0% | 0% |
| Compound No. Control 5 | 10% | 0% |
| Compound No. Control 6 | 20% | 0% |
| Compound No. Control 7 | 5% | 0% |

TABLE 4-continued

| Test compound | Insecticidal ratio (%)* | |
|---|---|---|
| | 10 ppm | 1 ppm |
| Compound No. Control 8 | 0% | 0% |
| Compound No. Control 9 | 0% | 0% |
| Compound No. Control 10 | 10% | 0% |
| Compound No. Control 11 | 15% | 0% |
| Compound No. Control 12 | 0% | 0% |
| Compound No. Control 13 | 0% | 0% |
| Compound No. Control 14 | 0% | 0% |
| Compound No. Control 15 | 0% | 0% |
| Compound No. Control 16 | 0% | 0% |
| Compound No. Control 17 | 0% | 0% |
| Compound No. Control 18 | 0% | 0% |
| Compound No. Control 19 | 10% | 0% |
| Compound No. Control 20 | 10% | 0% |
| Compound No. Control 21 | 15% | 0% |
| Compound No. Control 22 | 0% | 0% |
| Compound No. Control 23 | 5% | 0% |
| Compound No. Control 24 | 0% | 0% |
| Control C** | 0% | 0% |

$$*\text{Insecticidal ratio (\%)} = \frac{\text{Number of larvae released} - \text{Number of larvae at the time of investigation}}{\text{Number of the larvae released}} \times 100$$

**Control C = Chlorfluazuron

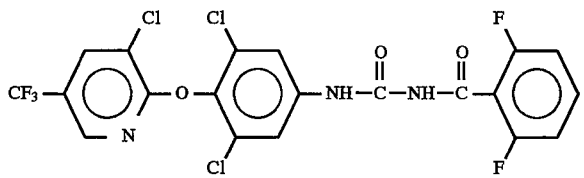

Test Example 3: Ovicidal Test on *Tetranychus kanzawai* Water was put in each of ice cream vessels (diameter 9 cm), a hole was made at a portion of the lid, a sheet of filter paper to which a strip shape of cut had been made was inserted thereinto to make the whole filter paper wet with water absorption, and leaves of kidney bean were put thereon. 20 Female imagoes of *Tetranychus kanzawai* were inoculated on the leaves on each sheet, and allowed to oviposit for 24 hours, and then removed. Chemicals of the stated concentrations (emulsions prepared according to Formulation example 1 were diluted with water) were applied, respectively, and the vessels were allowed to stand in a constant temperature chamber (25° C.). 8 Days later, the numbers of larvae hatched were investigated by a microscope, and ovicidal ratios were calculated. The test was carried out through three replicates for each section. The results are shown in the following Table 5.

TABLE 5

| Test compound | Ovicidal ratio (%)* | |
|---|---|---|
| | 10 ppm | 1 ppm |
| Compound No. 1 | 100% | 100% |
| Compound No. 2 | 100% | 100% |
| Compound No. 3 | 100% | 100% |
| Compound No. 4 | 100% | 100% |
| Compound No. 5 | 100% | 100% |
| Compound No. 6 | 100% | 100% |
| Compound No. 7 | 100% | 100% |
| Compound No. 8 | 100% | 100% |
| Compound No. 9 | 100% | 100% |
| Compound No. 10 | 100% | 100% |
| Compound No. 11 | 100% | 100% |
| Compound No. 12 | 100% | 100% |
| Compound No. 13 | 100% | 100% |

TABLE 5-continued

| Test compound | Ovicidal ratio (%)* | |
|---|---|---|
| | 10 ppm | 1 ppm |
| Compound No. 14 | 100% | 100% |
| Compound No. 15 | 100% | 100% |
| Compound No. 16 | 100% | 100% |
| Compound No. 17 | 100% | 100% |
| Compound No. 18 | 100% | 100% |
| Compound No. 19 | 100% | 100% |
| Compound No. 20 | 100% | 100% |
| Compound No. Control 1 | 0% | 0% |
| Compound No. Control 2 | 0% | 0% |
| Compound No. Control 3 | 30% | 5% |
| Compound No. Control 4 | 0% | 0% |
| Compound No. Control 5 | 0% | 0% |
| Compound No. Control 6 | 30% | 5% |
| Compound No. Control 7 | 0% | 0% |
| Compound No. Control 8 | 0% | 0% |
| Compound No. Control 9 | 30% | 5% |
| Compound No. Control 10 | 0% | 0% |
| Compound No. Control 11 | 0% | 0% |
| Compound No. Control 12 | 20% | 0% |
| Compound No. Control 13 | 30% | 0% |
| Compound No. Control 14 | 20% | 0% |
| Compound No. Control 15 | 0% | 0% |
| Compound No. Control 16 | 0% | 0% |
| Compound No. Control 17 | 20% | 0% |
| Compound No. Control 18 | 30% | 0% |
| Compound No. Control 19 | 20% | 0% |
| Compound No. Control 20 | 0% | 0% |
| Compound No. Control 21 | 0% | 0% |
| Compound No. Control 22 | 20% | 0% |
| Compound No. Control 23 | 30% | 0% |
| Compound No. Control 24 | 20% | 0% |
| Control D** | 0% | 0% |
| Control E*** | 0% | 0% |

*Ovicidal ratio (%) = $\frac{\text{Number of nits blown} - \text{Number of larvae hatched}}{\text{Number of nits blown}} \times 100$

**Control D = Hexythiazox

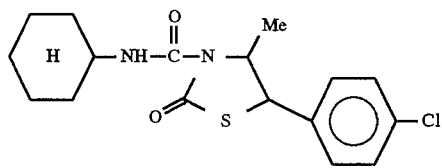

***Control E = Pyridaben

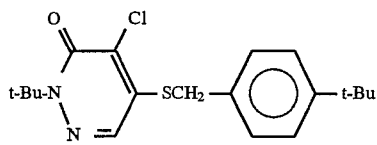

What is claimed is: 1. A composition for control of plant-parasitic insects and mites which comprises an insecticidally and miticidally effective amount of an oxazoline derivative represented by the formula

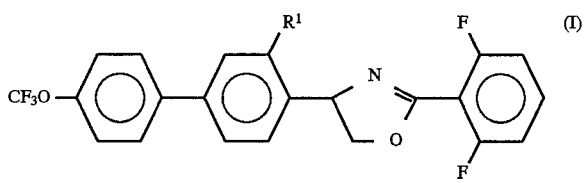

wherein $R^1$ represents a fluorine atom, a chlorine atom or a methyl group,
and agrohorticulturally acceptable adjuvants. 2. The composition according to claim 1 wherein, in the formula (I), $R^1$ represents a fluorine atom. 3. The composition according to claim 1 in a form of an emulsion, a flowable agent or wettable powder. 4. The composition according to claim 1 in a form of an emulsion. 5. The composition according to claim 1 which contains the compound of the formula (I) at a concentration within the range of 0.01 to 80 wt. %. 6. The composition according to claim 5 which contains the compound of the formula (I) at a concentration within the range of 0.01 to 50 wt. %. 7. The composition according to claim 6 which contains the compound of the formula (I) at a concentration within the range of 0.1 to 20 wt. %. 8. A method for controlling an insect or mite harmful to an agrohorticultural crop which comprises applying an insecticidally or miticidally effective amount of an oxazoline derivative represented by the formula

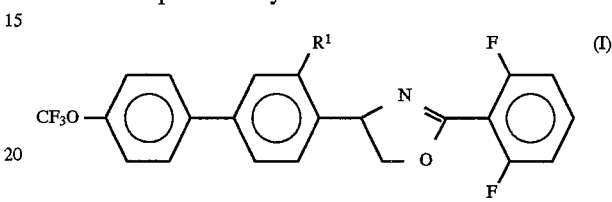

wherein $R^1$ represents a fluorine atom, a chlorine atom or a methyl group, directly to imagoes, larvae or nits of the insect or mite, or to a locus inhabited by the imagoes, larvae or nits. 9. A composition for control of plant-parasitic insects and mites in the form of an emulsion, flowable agent or wettable powder, which comprises 0.01 to 50% by weight of an oxazoline derivative represented by the formula

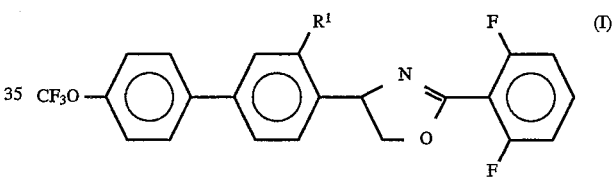

wherein $R^1$ represents a fluorine atom, a chlorine atom or a methyl group, and agrohorticulturally acceptable adjuvants. 10. The composition according to claim 9 which contains the compound of formula (I) at a concentration within the range of 0.1 to 20 wt. %. 11. A method for controlling an insect or mite harmful to an agrohorticultural crop which comprises applying a composition in the form of an emulsion, flowable agent or wettable powder, comprising 0.01 to 50% by weight of an oxazoline derivative represented by the formula

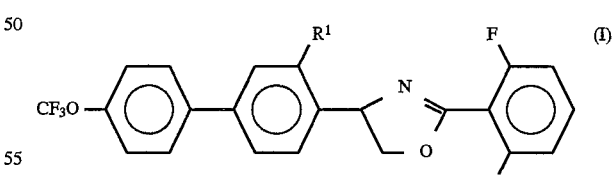

wherein $R^1$ represents a fluorine atom, a chlorine atom or a methyl group, and agrohorticulturally acceptable adjuvants, at a rate of 0.1 to 10 kg per hectare, directly to imagoes, larvae or nits of the insect or mite, or to a locus inhabited by the imagoes, larvae or nits. 12. The method according to claim 11 wherein the composition contains the compound of formula (I) at a concentration within the range of 0.1 to 20 wt. %.

* * * * *